United States Patent

Simon

(10) Patent No.: US 6,663,852 B2
(45) Date of Patent: Dec. 16, 2003

(54) METHOD AND MAKEUP KIT CONTAINING GONIOCHROMATIC AND MONOCHROMATIC PIGMENTS

(75) Inventor: Jean-Christophe Simon, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/218,405

(22) Filed: Aug. 15, 2002

(65) Prior Publication Data

US 2003/0012753 A1 Jan. 16, 2003

Related U.S. Application Data

(63) Continuation of application No. 09/289,817, filed on Apr. 12, 1999, now Pat. No. 6,451,294.

(30) Foreign Application Priority Data

Apr. 10, 1998 (FR) .............................................. 9804581

(51) Int. Cl.[7] .............................................. A61K 7/027
(52) U.S. Cl. .......................... 424/63; 424/401; 424/61; 424/64; 424/70.7; 424/600; 424/639; 424/642; 424/646; 424/648; 424/655; 424/682; 424/684
(58) Field of Search ............................. 424/63, 401, 61, 424/64, 70.7, 600, 639, 642, 646, 648, 655, 682, 684

(56) References Cited

U.S. PATENT DOCUMENTS 6,346,237 B2 * 2/2002 Lemann et al. ................ 424/61
6,451,294 B1 * 9/2002 Simon .......................... 424/63

FOREIGN PATENT DOCUMENTS

EP      0815826 A2 * 1/1998

* cited by examiner

Primary Examiner—Thurman K. Page
Assistant Examiner—Liliana Di Nola-Baron
(74) Attorney, Agent, or Firm—Oblon, Spivak, McClelland, Maier & Neustadt, P.C.

(57) ABSTRACT

The present invention relates to a new makeup kit comprising a first, goniochromatic pigment composition which is intended to form a base layer and a second, conventional pigment composition having one of the colors of the first pigment, the second composition being intended to form a surface layer comprising decorative motifs. Depending on the viewing angle, therefore, it is possible to see the said motifs appear or disappear. This kit is intended in particular for making up the nails, lips, cheeks or eyelids, or else the body. The invention also relates to a method of making up the human face, lips or body.

35 Claims, 1 Drawing Sheet

METHOD AND MAKEUP KIT CONTAINING GONIOCHROMATIC AND MONOCHROMATIC PIGMENTS

BACKGROUND OF THE INVENTION

The present invention relates to a cosmetic product, a makeup kit containing the product, and a method of making up the human body using the cosmetic product.

SUMMARY OF THE INVENTION

The present invention relates to a makeup kit intended for a novel type of makeup combining a first, goniochromatic pigment and a second pigment, especially a monochromatic pigment, having one of the colors of the first pigment. This kit comprises two cosmetic makeup compositions which can be applied to the skin on both the face and other parts of the human body, to the lips and to the exoskeletal appendages such as the nails, eyelashes, eyebrows or hair. The invention also relates to a bilayer makeup method.

Each composition can be a loose or compact powder, a foundation, a rouge or eyeshadow, a concealer, a blusher, a lipstick, a lip or eye pencil, or else a nail varnish, or a body makeup product.

The makeup compositions consist of a suitable vehicle and various colorants which are intended to impart a certain color to the compositions before and/or after their application to the skin, lips or exoskeletal appendages.

DISCUSSION OF THE BACKGROUND

The range of colorants employed at present by cosmeticians is fairly limited; they are mainly organic pigments, lakes, inorganic pigments and pearlescent pigments. The lakes allow the production of vivid colors but are for the most part unstable to light, heat and pH. Some of them have the further disadvantage of unsightly marking of the skin after application owing to emergence of the dye. The inorganic pigments, especially the inorganic oxides, on the other hand, are highly stable but give colors which tend to be dull and pale. The pearlescent pigments, for their part, allow the production of colors which are varied but never intense, with iridescent effects which are, however, usually weak.

To overcome these disadvantages, the Applicant envisaged using goniochromatic pigments; that is, pigments which have colors that vary depending on the viewing angle and light incidence and which impart iridescent effects in somewhat the same way as a pearlescent product. Reference may be made in particular to the application EP-A-815826.

Certain conventional makeup products, moreover, allow the creation of decorative effects with colored motifs: drawings, chequered patterns, letters, etc. However, these motifs are visible at any viewing angle, so making the makeup "static".

With makeup artists and consumers looking more and more for special effects and original colors, the Applicant has discovered a novel type of makeup using goniochromatic pigments. By using a bilayer product whose underlayer contains at least one goniochromatic pigment, the Applicant has found, surprisingly, that it is possible to trace or draw motifs on such a layer (letters, drawings, chequered patterns, etc.), in particular with a pencil or fine brush, and that, depending on the direction from which they are observed, the motifs appear or disappear. The invention has a novel makeup effect: the colored motifs appear and disappear in accordance with the movements of the person wearing the makeup. The makeup therefore appears to be "alive".

Figure 1:
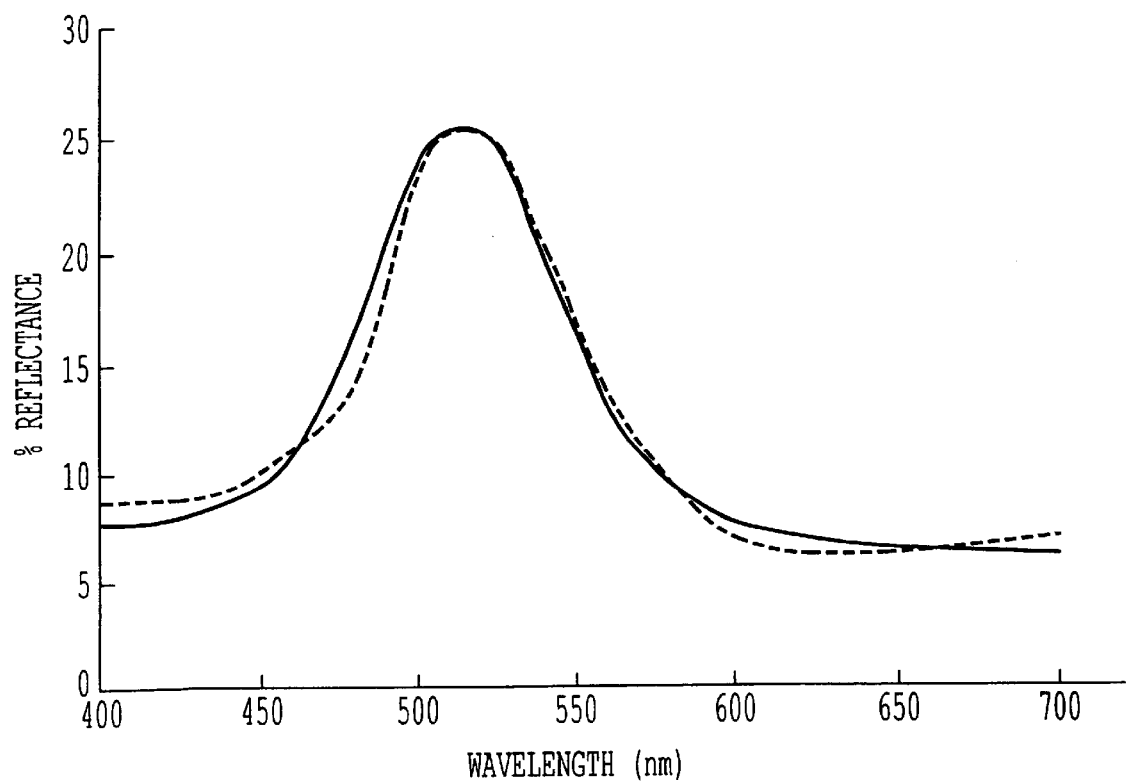
FIG. 1 shows the reflectance of the varnish layers 1 and 2 expressed as a percentage (% of light transmitted) as a function of the wavelength expressed in nm. This reflectance was measured in accordance with observation perpendicular to the layers 1 and 2. The solid line is the reflectance of layer 1 and the dashed line is the reflectance of layer 2.

These curves clearly indicate that the color obtained for the two layers is the same in the direction perpendicular to the layers and that there is no metamerism: that is, a change in color depending on the nature of illumination. Therefore, viewed in natural light, the makeup will be identical to that viewed in artificial light.

DETAILED DESCRIPTION OF THE INVENTION

The invention more specifically provides a makeup kit comprising a first composition comprising a cosmetically acceptable medium and at least one first colorant and a second composition comprising a cosmetically acceptable medium and at least one second colorant, one of the colorants being a goniochromatic colorant which is able to produce different colors depending on the light incidence and viewing angle and the other a monochromatic colorant which produces one of the colors of the goniochromatic colorant.

The invention additionally provides a method of making up the human skin, lips and/or exoskeletal appendages, which comprises applying to the skin, lips and/or exoskeletal appendages a first layer of a first composition comprising a cosmetically acceptable medium and at least one first colorant and then applying to part of the said first layer a second layer of a second composition comprising a cosmetically acceptable medium and at least one second colorant, one of the first and second colorants being a goniochromatic colorant able to produce different colors depending on the light incidence and the viewing angle and the other colorant being a monochromatic colorant which produces one of the colors of the goniochromatic colorant.

The document WO-A-96/39307 from Flex Products describes a combination of two layers of motifs, each layer comprising goniochromatic pigments, which can be used in inks and automotive finishes. This document does not envisage the use of this combination to obtain an original makeup form nor the replacement of one of the goniochromatic pigments by conventional monochromatic pigments giving a color identical to one of the colors of the goniochromatic layer.

The invention additionally provides a cosmetic makeup product comprising a cosmetically acceptable medium, at least one first colorant and at least one second colorant, one of the first and second colorants being a goniochromatic colorant able to produce different colors depending on the light incidence and viewing angle and the other being a monochromatic colorant which produces one of the colors of the goniochromatic colorant. Preferably, the first and second colorants are packaged separately in, respectively, first and second cosmetically acceptable compositions.

Advantageously, these two compositions are packaged in separate compartments or containers and are accompanied by appropriate means of application.

According to the invention, the second layer is applied to only part of the first layer. It can be applied alternatively to one of the ends of the first layer, or in the middle, or else discontinuously, in particular in the form of geometric, symmetric or asymmetric motifs (for example, in the form of dots, squares, circles, stars, alphanumeric inscriptions or any other symbol, figurative or otherwise) which are in random or ordered distribution and have sharp or fuzzy outlines. Hence, at one viewing angle, especially perpendicular to the second layer, the motifs of this second layer will disappear, because their color will be identical to that of the goniochromatic layer, and, in the other directions, the motifs will appear because of their different color from that of the first layer.

The first colorant is preferably the goniochromatic colorant and the second the monochromatic colorant, although the reverse is possible.

This bilayer architecture can be adapted for all makeup products for the skin as well as for the face, scalp and body, the mucosae such as the lips and the inside of the lower eyelids, and the exoskeletal appendages such as the nails, eyelashes, eyebrows and the hair—on the head or even elsewhere. The second layer, which forms motifs, can be applied with a pen, pencil or any other instrument (sponge, finger, coarse or fine brush, quill, nib, etc.). This architecture may also be applied to makeup accessories such as false nails, false eyelashes, hairpieces, or else discs or patches which adhere to the skin or lips (of the beauty-spot type).

The invention additionally relates to a made-up substrate comprising a first layer of a first composition comprising at least one first colorant and a second layer of a second composition deposited in part on the first layer and comprising at least one second colorant, one of the colorants being a goniochromatic colorant able to produce different colors depending on the light incidence and viewing angle and the other colorant being a monochromatic colorant which produces one of the colors of the goniochromatic colorant.

The invention also provides a cosmetic composition for implementing the above makeup method. This composition comprises a cosmetically acceptable medium and at least one goniochromatic colorant able to produce different colors depending on the light incidence and viewing angle, the colorant being selected advantageously from multilayer interference structures.

The first (or second) composition of the invention may comprise one or more goniochromatic colorants selected from mesomorphoric and liquid-crystal (LC) colorants and multilayer interference structures. Preference is given to using a single goniochromatic colorant on account of ease of use and low production cost.

The LC colorants are, in particular, linear or cyclic monomers or polymers onto which mesomorphic groups are grafted, especially cholesteric or nematic groups. The LC colorants comprise, for example, silicones or cellulose ethers onto which mesomorphic groups are grafted. The LC colorants are selected in particular from cyclic organopolysiloxanes grafted with cholesteric and biphenyl-type groups. These grafted organopolysiloxanes are, in particular, crosslinked in accordance with a three-dimensional structure.

The LC colorants are selected in particular from cyclic silicones of the formula:

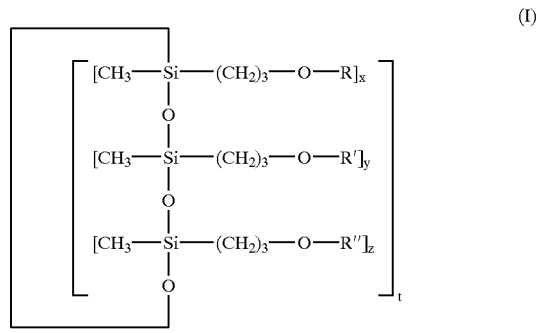
(I)

in which:
$0 \leq x \leq 1$ (preferably 1); $0 \leq y \leq 1$ (preferably 1); $0 \leq z \leq 1$ (preferably 1) where $x+y+z \neq 0$; $3 \leq t = 10$;
R denotes a group of the following formula:

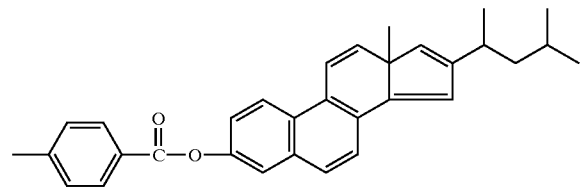

R' denotes a group of the following formula:

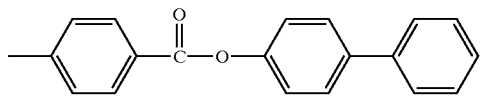

and
R" denotes a group of the following formula:

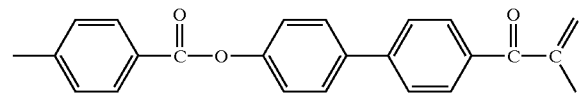

These compounds are generally present in the form of amorphous white powders. They have the particular feature of exhibiting the observation-direction-dependent color change effect only as a function of the substrate (and, in particular, its color) on which they are spread.

As examples of LC colorants meeting this definition, mention may be made in particular of the "LC" pigments from the company Wacker which are called SLM 41101 (blue/green), SLM 41102 (red/gold) and SLM 41103 (yellow/green), and LC PIGMENT GRUN 516 S VP (blue/green) (see also the document EP-A-815826).

Goniochromatic colorants with multilayer structures are, in particular, those described in the following documents: U.S. Pat. No. 3,438,796, EP-A-227423, U.S. Pat. No. 5,135,812, EP-A-170439, EP-A-341002, U.S. Pat. Nos. 4,930,866, 5,641,719, EP-A-472371, EP-A-395410, EP-A-753545, EP-A-768343, EP-A-571836, EP-A-708154, EP-A-579091, U.S. Pat. Nos. 5,411,586, 5,364,467, WO-A-97/39066, DE-A-4 225 031, WO 9517479 (BASF), and DE-A-196 14 637. They are in the form of flakes with a metallic color.

The multilayer structures which can be used in the invention are, for example, the following structures: $Al/SiO_2/Al/SiO_2/Al$; $Cr/MgF_2/Al/MgF_2/Al$; $MoS_2/SiO_2/Al/SiO_2/MoS_2$; $Fe_2O_3/SiO_2/Al/SiO_2/Fe_2O_3$; $Fe_2O_3/SiO_2/Fe_2O_3/SiO_2/$ $Fe_2O_3$; $MoS_2/SiO_2$/oxide mica/$SiO_2/MoS_2$; $Fe_2O_3/SiO_2$/oxide mica/$SiO_2/Fe_2O_3$. Different colors are obtained depending on the thickness of the various layers. Thus with the structure $Fe_2O_3/SiO_2/Al/SiO_2/Fe_2O_3$ the range is from greenish gold to reddish grey for $SiO_2$ layers of 320 to 350 nm; from red to gold for $SiO_2$ layers of 380 to 400 nm; from violet to green for $SiO_2$ layers of 410 to 420 nm; and from copper to red for $SiO_2$ layers of 430 to 440 nm.

It is also possible to use birefringent multilayer structures comprising an alternating sequence of polymeric layers of the polyethylene naphthalate and polyethylene terephthalate type, as described in the document WO-A-96/19347.

The second (or first) composition of the invention may comprise one or more monochromatic colorants selected from monochromatic dyes, monochromatic pigments and nacreous pigments which are conventionally employed in cosmetic compositions, and combinations thereof. According to the invention, the assembly of these colorants must exhibit one of the colors of the goniochromatic colorant or of the assembly of goniochromatic colorants.

By pigments is meant white or colored, organic or inorganic particles which are insoluble in the liquid fatty phase and are intended for coloring and/or opacifying the second composition. By nacreous pigments are meant iridescent particles, produced in particular by certain molluscs in their shell, or else synthesized. By dyes are meant compounds, generally organic, which are soluble in fatty substances such as oils or in an aqueous-alcoholic phase.

The colorants of the first and second layers can be present in a proportion of from 0.01 to 60% of the total weight, respectively, of the first composition and second composition, preferably from 0.05 to 30% and, more particularly, from 1 to 20%, for non-pulverulent compositions. For pulverulent compositions, the amount of colorants can be up to 85% or even up to 98%.

As monochromatic inorganic pigments which can be used in the invention, mention may be made of titanium oxide, zirconium oxide, and of cerium oxide, and also zinc oxide, iron oxide and chromium oxide, and iron blue. Among organic pigments which can be used in the invention, mention may be made of carbon black and barium, strontium, calcium and aluminum lakes.

The dyes can be fat-soluble or water-soluble. Fat-soluble dyes are, for example, Sudan Red, DC Red 17, DC Green 6, β-carotene, soya oil, Sudan Brown, DC Yellow 11, DC Violet 2, DC Orange 5, and Quinoline Yellow. They can represent from 0.01 to 20% of the total weight of the second composition and, more preferably, from 0.1 to 10%. The water-soluble dyes are, in particular, copper sulphate, iron sulphate, water-soluble sulphopolyesters such as those described in the document FR-96 154152, rhodamines, natural dyes (carotene, beetroot juice) and Methylene Blue.

The nacreous pigments can be present in the second composition in a proportion of from 0 to 20% of the total weight of the said second composition, preferably in an amount of the order of from 1 to 15%. Among nacreous pigments which can be used in the second composition, mention may be made of mica coated with titanium dioxide, with iron oxide, with natural pigment or with bismuth oxychloride, such as colored titanium mica.

The first and second compositions according to the invention can, moreover, comprise all of the ingredients which are conventionally employed in the fields in question and, more specifically, in the fields of cosmetology and dermatology. These ingredients are selected in particular from preservatives, stabilizers, neutralizing agents, aqueous-phase thickeners (polysaccharide biopolymers, synthetic polymers) or fatty-phase thickeners, such as clay minerals, fillers, perfumes, hydrophilic or lipophilic active substances, surfactants, antioxidants, film-forming polymers and mixtures thereof. The amounts of these various ingredients are those conventionally employed in the fields in question and, for example, from 0.01 to 30% of the total weight of the composition. The nature of these ingredients and their proportion must be compatible with the production of compositions according to the invention which are stable, thickened and bright. The composition can also comprise water in a concentration of from 0 to 95% of the total weight of the composition, or organic solvents, which can represent up to 90%.

By fillers are meant lamellar or non-lamellar, synthetic or inorganic, white or colorless particles. These fillers can be introduced into the first or second layers in order, in particular, to modify the texture of these compositions. They can be present in a proportion of from 0 to 35% of the total weight of each composition, preferably from 0.5 to 15%. Mention may be made in particular of talc, zinc stearate, mica, kaolin, nylon powders (especially Orgasol) and polyethylene powders, Teflon, starch, boron nitride, copolymer microspheres such as Expancel (Nobel Industrie), polytrap (Dow Corning), and silicone resin microbeads (Tospearl from Toshiba, for example), or else silica.

The first and second compositions of the invention advantageously comprise a fatty phase containing fatty substances which are liquid, solid or pastelike at room temperature. The fatty substances which are solid at room temperature permit structuring of the composition; they are selected from gums and/or waxes. The waxes can be hydrocarbon waxes, fluoro waxes and/or silicone waxes and can be vegetable, mineral, animal and/or synthetic in origin. In particular, the waxes have a melting point of more than 25° C. and, more preferably, more than 45° C.

As waxes which can be used in the first and second compositions of the invention, mention may be made of lanolin, beeswax, carnauba wax or candellila wax, paraffin, lignite waxes, microcrystalline waxes, ceresin or ozocerite; synthetic waxes, such as polyethylene waxes, Fischer-Tropsch waxes, and silicone waxes such as the alkyl- or alkoxydimethicones having 16 to 45 carbon atoms.

The gums are, in particular, organopolysiloxanes having an average molecular weight of from 1000 to 500,000.

The nature and amount of these gums and waxes depend on the desired textural and mechanical properties. By way of indication, each composition can contain from 0 to 50% by weight of waxes relative to the total weight of the composition and, more preferably, from 5 to 30%.

As fatty substances which are liquid at room temperature and can be used in the compositions of the invention, mention may be made of:

hydrocarbon oils of animal origin, such as perhydrosqualene;

vegetable hydrocarbon oils, such as the liquid triglycerides of fatty acids with 4 to 10 carbon atoms, such as the triglycerides of heptanoic or octanoic acid, or else sunflower oil, maize oil, soya oil, marrow oil, grapeseed oil, sesame oil, hazelnut oil, apricot oil, macadamia oil, castor oil and avocado oil, the triglycerides of caprylic/capric acids such as those sold by the company Stéarineries Dubois or those sold under the names Miglyol 810, 812 and 818 by the company Dynamit Nobel, jojoba oil, karite butter;

linear or branched hydrocarbons of mineral or synthetic origin, such as liquid paraffins and their derivatives, vaseline, polydecenes, hydrogenated polyisobutene

- such as parleam; isoparaffins such as isohexadecane and isodecane;
- synthetic ethers and esters, especially those of fatty acids, such as oils of formula $R_1COOR_2$ in which $R_1$ represents the radical of a higher fatty acid having from 7 to 29 carbon atoms and $R_2$ represents a hydrocarbon chain containing from 3 to 30 carbon atoms, such as, for example, purcellin oil, isopropyl myristate, 2-ethylhexyl palmitate, 2-octyldodecyl stearate, 2-octyldodecyl erucate and isostearyl isostearate; hydroxylated esters, such as isostearyl lactate, octyl hydroxystearate, octyldodecyl hydroxystearate, diisostearyl malate, triisocetyl citrate and fatty alcohol heptanoates, octanoates and decanoates; polyol esters, such as propylene glycol dioctanoate, neopentyl glycol diheptanoate and diethylene glycol diisononanoate; and the esters of pentaerythritol;
- fatty alcohols having from 12 to 26 carbon atoms, such as octyldodecanol, 2-butyloctanol, 2-hexyldecanol, 2-undecylpentadecanol and oleyl alcohol;
- partially fluorinated hydrocarbon and/or silicone oils, such as those described in the document JP-A-2-295912;
- silicone oils such as polymethylsiloxanes (PDMS), volatile or otherwise, linear or cyclic and liquid or pastelike at room temperature; phenylated silicones such as phenyltrimethicones, diphenyldimethicones, phenyldimethicones and phenyltrimethylsiloxydiphenylsiloxanes;
- fluorinated oils and fluorosilicone oils; and
- mixtures thereof.

These oils can represent from 0 to 99.9% of the total weight of each composition.

As volatile silicone oils which can be used in the invention, mention may be made of linear or cyclic silicones having from 2 to 7 silicon atoms, these silicones optionally containing alkyl groups having from 1 to 10 carbon atoms. These silicones are therefore, in particular, hexamethyldisiloxane and cyclopenta- or cyclotetra- or cyclohexadimethylsiloxane. These volatile oils can represent from 0 to 50% of the total weight of the composition.

As solvents which can be used in the invention, mention may be made of:
- ketones which are liquid at room temperature, such as methyl ethyl ketone, methyl isobutyl ketone, diisobutyl ketone, isophorone, cyclohexanone and acetone;
- alcohols which are liquid at room temperature, such as ethanol, isopropanol, diacetone alcohol, 2-butoxyethanol and cyclohexanol;
- glycols which are liquid at room temperature, such as ethylene glycol, propylene glycol and pentylene glycol;
- propylene glycol ethers which are liquid at room temperature, such as propylene glycol monomethyl ether, propylene glycol monomethyl acetate and dipropylene glycol mono-n-butyl ether;
- short-chain esters (having from 3 to 8 carbon atoms in total) such as ethyl acetate, methyl acetate, propyl acetate, n-butyl acetate and isopentyl acetate;
- ethers which are liquid at room temperature, such as diethyl ether, dimethyl ether and dichlorodiethyl ether;
- alkanes which are liquid at room temperature, such as decane, heptane, dodecane and cyclohexane;
- cyclic aromatic compounds which are liquid at room temperature, such as toluene and xylene; and
- aldehydes which are liquid at room temperature, such as benzaldehyde and acetaldehyde.

These solvents are especially suitable for nailcare and nail makeup: the composition in that case constitutes a nail varnish or a nail care product. Other solvents which can be used include water and aqueous-alcohol media.

As film-forming polymers which can be used in the invention, mention may be made of nitrocellulose, cellulose acetobutyrate, polyvinylbutyrals, alkyd resins, resins resulting from the condensation of formaldehyde with an arylsulphonamide, polyesters, polyurethanes, polyester-polyurethanes, polyether-polyurethanes, radical polymers, in particular of the acrylic, styrene-acrylic and/or vinyl type, and mixtures thereof.

The polymers can be dissolved or dispersed in the composition. They can generally be present at a level ranging from 0.5 to 40% by weight relative to the total weight of the composition and, more preferably, ranging from 10 to 20% by weight.

In addition to the film-forming polymer or polymers, the composition according to the invention can also comprise plasticizers which allow the flexibility of the polymer film to be adjusted without lessening its physical strength. Plasticizers which can be used are those commonly employed in nail varnish compositions. Plasticizers which may be mentioned are dibutyl phthalate, dioctyl phthalate, diisobutyl phthalate and dimethoxyethyl phthalate, benzyl benzoate and glyceryl benzoate; triethyl citrate, tributyl citrate and tributyl acetyl citrate; tributyl phosphate and triphenyl phosphate; glycols; camphor, and derivatives and mixtures thereof. The plasticizers can be present in general at a level ranging from 1 to 30% by weight relative to the total weight of the composition and, more preferably, from 5 to 10% by weight.

The compositions of the invention can be present in any of the pharmaceutical forms which are normally employed for topical application, and, in particular, in the form of an aqueous or oily solution, an aqueous or oily gel, an oil-in-water or water-in-oil emulsion, a vesicular dispersion of oil in water, the vesicles being situated at the oil/water interface, or else a powder. Each composition may have the appearance of a lotion, cream, pomade, easily worked paste, ointment, a cast or molded solid, especially a stick or small cup, or else a compacted solid.

The product according to the invention can be advantageously used for making up the skin and/or mucosae and/or exoskeletal appendages, depending on the nature of the ingredients used. In particular, each composition of the invention may be in the form of a lipstick or lip gloss paste, a solid foundation, a concealer or eye-contour product, eyeliner, mascara, eyeshadow, aqueous or solvent-based nail varnish, a body makeup product or else a skin coloring product. These compositions may, furthermore, comprise cosmetic or dermatological active substances for the purpose, in particular, of imparting a beauty or treatment aspect to the composition. Hence these compositions may comprise vitamins and other lipophilic active substances (lanolin, UVA screen) or hydrophilic active substances (moisturizers such as glycerin).

The invention also relates to a lip product, foundation, tattoo, nail varnish, blusher or eyeshadow comprising a cosmetically acceptable medium and first and second compositions as described above.

The invention also provides for the use of the above cosmetic product for making motifs on the human skin and/or lips and/or exoskeletal appendages appear or disappear depending on the viewing angle.

The compositions of the invention can be obtained by heating the various constituents at the melting point of the highest waxes and then casting the molten mixture in a mold (dish or glove finger). They may also be obtained by extrusion as described in the application EP-A-667 146.

EXAMPLES

The following composition examples are given by way of illustration and without any limitative nature. The quantities given therein are in % by weight.

Exemplary Embodiment: Nail Varnish a) The varnish base (called VAO base) used for the two layers is as follows:

| | |
|---|---:|
| aliphatic polyurethane (film former) | 33.9 g |
| N-methylpyrrolidone (stabilizer) | 8.2 g |
| triethylamine (neutralizing agent) | 1.9 g |
| tributyl acetylcitrate | 3.2 g |
| water | q.s. 100 g | b) The composition for forming the first nail varnish layer 1 is produced with:

| | |
|---|---:|
| VAO base | 95 g |
| Wacker LC Pigments LC PIGMENT GRUN 516 S VP | 5 g |

This composition is obtained by mixing the VAO base and the pigments with stirring at room temperature. Its color changes depending on the viewing angle and varies from dark blue to dark green. This composition is applied continuously to nails without makeup, in the form of a single layer.

c) The composition for forming the second nail varnish layer 2 is composed of:

| | |
|---|---:|
| VAO base | 90.00 g |
| 60% aqueous dispersion of titanium dioxide (C.I. 77891) in a water/glycerol/surfactant mixture (16/18/5) | 4.73 g |
| 40% dispersion of Permanent Carmine FB in a water/glycerol/sodium lauryl ether sulphate mixture (29.7/25/5) | 0.13 g |
| 42% aqueous dispersion of Hansa Yellow G (C.I. 11680) in a water/glycerol/sodium lauryl ether sulphate mixture (27.7/25/5) | 1.51 g |
| 48% dispersion of Phthalocyanine Green FB (C.I. 74260) in a water/glycerol/sodium lauryl ether sulphate mixture (21.7/25/5) | 3.63 g |
| preservatives | q.s. |

The composition of layer 2 has a green color which is identical to one of the colors of the composition of layer 1. This composition is obtained by mixing the pigments and the VAO base in the manner conventional for producing a varnish.

This composition is applied by brush to the layer 1 to form motifs (dots, stars, butterflies). After the two-layer varnish has dried, it reveals only a homogeneous green color of the nail when viewed in a direction perpendicular to the surface (or the nail surface) and reveals green motifs against a blue background when viewed in a different direction.

The priority document of the present application, French patent 9804581 filed Apr. 10, 1998, is incorporated herein by reference.

Obviously, additional modifications and variations of the present invention are possible in light of the above teachings. It is therefore to be understood that within the scope of the appended claims, the invention may be practiced otherwise than as specifically described herein.

What is claimed is:

1. A cosmetic composition comprising:
a cosmetically acceptable medium;
at least one first colorant; and
at least one second colorant;
wherein said first colorant is a goniochromatic colorant able to produce different colors depending on the light incidence and viewing angle, said goniochromatic colorant being a multilayer interference structure, and said second colorant is a monochromatic colorant which produces one of the colors of said goniochromatic colorant.

2. The composition according to claim 1, wherein said goniochromatic colorant comprises a multilayer interference structure selected the group consisting of $Al/SiO_2/Al/SiO_2/Al$; $Cr/MgF_2/Al/MgF_2/Al$; $MoS_2/SiO_2/Al/SiO_2/MoS_2$; $Fe_2O_3/SiO_2/Al/SiO_2/Fe_2O_3$; $Fe_2O_3/SiO_2/Fe_2O_3/SiO_2/Fe_2O_3$; $MoS_2/SiO_2/$oxide mica$/SiO_2/MoS_2$; and $Fe_2O_3/SiO_2/$oxide mica$/SiO_2/Fe_2O_3$.

3. The composition according to claim 1, wherein said monochromatic colorant is selected from the group consisting of monochromatic dyes, monochromatic pigments, nacreous pigments, and mixtures thereof.

4. The composition according to claim 1, wherein said monochromatic colorant is selected from the group consisting of titanium oxide, zirconium oxide, cerium oxide, zinc oxide, iron oxides, chromium oxide, iron blue, carbon black; barium, strontium, calcium and aluminum lakes; Sudan Red, DC Red 17, DC Green 6, β-carotene, soya oil, Sudan Brown, DC Yellow 11, DC Violet 2, DC Orange 5, Quinoline Yellow; mica coated with titanium oxide, with iron oxide, with natural pigment, bismuth oxychloride, and colored titanium mica.

5. The composition according to claim 1, wherein each said colorant represents from 0.01 to 98% of the total weight of the product.

6. The composition according to claim 1, wherein each said colorant represents from 0.05 to 85% of the total weight of the product.

7. The composition according to claim 1, wherein said cosmetic composition is in the form of foundation, nail varnish, a body makeup product, lip makeup product, blusher or eyeshadow.

8. The composition according to claim 1, wherein said first and second colorants are packaged, respectively, in first and second compositions each comprising a cosmetically acceptable medium.

9. The composition according to claim 1, wherein said cosmetic composition is in a form selected from the group consisting of an oily solution, an aqueous solution, an oily gel, an aqueous gel, an oil-in-water emulsion, a water-in-oil emulsion, a vesicular dispersion of oil in water wherein the vesicles are located at the oil/water interface, and a powder.

10. The composition according to claim 1, wherein said cosmetically acceptable medium contains at least one ingredient selected from the group consisting of oils, solvents, waxes, film-forming polymers, fillers, hydrophilic or lipophilic active substances, aqueous-phase thickeners, fatty-phase thickeners, surfactants, antioxidants, perfumes, plasticizers, neutralizing agents, stabilizers, and mixtures thereof.

11. A method of making up the human skin, lips and/or exoskeletal appendages, which comprises:

applying to a substrate a first layer of a first composition; and applying on said first layer a second layer of a second composition;

wherein said substrate is selected from the group consisting of skin, lips and/or exoskeletal appendages, said first composition comprises a cosmetically acceptable medium and at least one first colorant and the second composition comprises a cosmetically acceptable medium and at least one second colorant; wherein at least one of said first or one of said second colorants is a goniochromatic colorant able to produce different colors depending on the light incidence and the viewing angle, said goniochromatic colorant being a multilayer interference structure, and the other colorant is a monochromatic colorant which produces one of the colors of the goniochromatic colorant.

12. The method according to claim 11, wherein said second layer is discontinuous.

13. The method according to claim 11, wherein said second layer comprises motifs.

14. The method according to claims 13, wherein said motifs are distributed randomly, symmetrically or asymmetrically on said second layer.

15. The method according to claim 11, wherein said goniochromatic colorant comprises a multilayer interference structure selected from the group consisting of $Al/SiO_2/Al/SiO_2/Al$; $Cr/MgF_2/Al/MgF_2/Al$; $MoS_2/SiO_2/Al/SiO_2/MoS_2$; $Fe_2O_3/SiO_2/Al/SiO_2/Fe_2O_3$; $Fe_2O_3/SiO_2/Fe_2O_3/SiO_2/Fe_2O_3$; $MoS_2/SiO_2/$oxide mica/$SiO_2/MoS_2$; and $Fe_2O_3/SiO_2/$oxide mica/$SiO_2/Fe_2O_3$.

16. The method according to claim 13, wherein said monochromatic colorant is selected from the group consisting of monochromatic dyes, monochromatic pigments, nacreous pigments, and mixtures thereof.

17. The method according to claim 16, wherein said monochromatic colorant is selected from titanium oxide, zirconium oxide, cerium oxide, zinc oxide, iron oxide, chromium oxide, iron blue, carbon black; barium, strontium, calcium and aluminum lakes; Sudan Red, DC Red 17, DC Green 6, β-carotene, soya oil, Sudan Brown, DC Yellow 11, DC Violet 2, DC Orange 5, Quinoline Yellow; mica coated with titanium oxide, iron oxide, natural pigment, bismuth oxychloride, or colored titanium mica.

18. A makeup kit comprising:
a first composition comprising a cosmetically acceptable medium and at least one first colorant; and
a second composition comprising a cosmetically acceptable medium and at least one second colorant;
wherein one of said first colorants is a goniochromatic colorant which is able to produce different colors depending on the light incidence and viewing angle, said goniochromatic colorant being a multilayer interference structure, and said second colorant is a monochromatic colorant which produces one of the colors of the goniochromatic colorant.

19. The makeup kit according to claim 18, wherein said first and second colorants are packaged separately in, respectively, first and second compositions comprising a cosmetically acceptable medium.

20. The makeup kit according to claim 18, wherein said colorant having a multilayer structure is selected from the group consisting of $Al/SiO_2/Al/SiO_2/Al$; $Cr/MgF_2/Al/MgF_2/Al$; $MoS_2/SiO_2/Al/SiO_2/MoS_2$; $Fe_2O_3/SiO_2/Al/SiO_2/Fe_2O_3$; $Fe_2O_3/SiO_2/Fe_2O_3/SiO_2/Fe_2O_3$; $MoS_2/SiO_2/$oxide mica/$SiO_2/MoS_2$; and $Fe_2O_3/SiO_2/$oxide mica/$SiO_2/Fe_2O_3$.

21. The makeup kit according to claim 18, wherein said monochromatic colorant is selected from the group consisting of monochromatic dyes, monochromatic pigments, nacreous pigments, and mixtures thereof.

22. The makeup kit according to claim 18, wherein the monochromatic colorant is selected from the group consisting of titanium oxide, zirconium oxide, cerium oxide, zinc oxide, iron oxide, chromium oxide, iron blue, carbon black; barium, strontium, calcium and aluminum lakes; Sudan Red, DC Red 17, DC Green 6, β-carotene, soya oil, Sudan Brown, DC Yellow 11, DC Violet 2, DC Orange 5, Quinoline Yellow; mica coated with titanium oxide, iron oxide, natural pigment, bismuth oxychloride, and colored titanium mica.

23. The makeup kit according to claim 18, wherein said makeup kit further comprises applicators for applying the first and second compositions to the skin, mucosae, exoskeletal appendages and combinations thereof.

24. The makeup kit according to claim 23, wherein said applicators are selected from the group consisting of fine and coarse brushes, stylos, pens, quills, nibs and pencils.

25. The makeup kit according to one of claim 18, wherein said first and second compositions are packaged in separate compartments or containers.

26. The makeup kit according to claim 18, wherein said cosmetically acceptable medium contains at least one ingredient selected from the group consisting of oils, solvents, waxes, film-forming polymers, fillers, hydrophilic active substances, lipophilic active substances, aqueous-phase thickeners, fatty-phase thickeners, surfactants, antioxidants, perfumes, plasticizers, neutralizing agents and stabilizers.

27. The makeup kit according to claim 18, wherein said compositions are in a form selected from the group consisting of an oily solution, an aqueous solution, an oily gel, an aqueous gel, oil-in-water emulsion, water-in-oil emulsion, powder, and a vesicular dispersion of oil in water, wherein said vesicles are located at the oil/water interface.

28. The makeup kit according to claim 18, wherein said compositions are in a form selected from the group consisting of foundation, nail varnish, a body makeup product, a lip makeup product, blusher, and eyeshadow.

29. One or more colored motifs on human skin, lips, mucosae, exoskeletal appendages or combinations thereof, prepared by the method of claim 11.

30. A composition comprising:
a cosmetically acceptable medium; and
at least one goniochromatic colorant able to produce different colors depending on the light incidence and viewing angle, said goniochromatic colorant being a multilayer interference structure.

31. The composition according to claim 30, wherein said multilayer interference structure is selected the group consisting of the structures $Al/SiO_2/Al/SiO_2/Al$; $Cr/MgF_2/Al/MgF_2/Al$; $Fe_2O_3/SiO_2/Al/SiO_2/Fe_2O_3$; $Fe_2O_3/SiO_2/Fe_2O_3/SiO_2/Fe_2O_3$; $MoS_2/SiO_2/$oxide mica/$SiO_2/MoS_2$; and $Fe_2O_3/SiO_2/$oxide mica/$SiO_2/Fe_2O_3$.

32. A made-up substrate comprising:

a first layer of a first composition further comprising at least one first colorant; and a second layer of a second composition deposited on the first layer and further comprising at least one second colorant;

wherein one of said first or second colorants is a goniochromatic colorant able to produce different colors depending on the light incidence and viewing angle, said goniochromatic colorant being a multilayer interference structure, and wherein the other colorant is a monochromatic colorant which produces one of the colors of the goniochromatic colorant.

33. The made-up substrate according to claim 32, wherein said made-up substrate is in a form selected from the group of false nails, false eyelashes and hairpieces.

34. The made-up substrate according to claim 32, wherein the second layer is discontinuous.

35. The made-up substrate according to claim 32, wherein the second layer comprises motifs in random or ordered distribution.

* * * * *